United States Patent [19]

Diamond et al.

[11] 4,115,564
[45] Sep. 19, 1978

[54] TREATMENT OF DIARRHEA WITH AMIDINOUREAS

[75] Inventors: Julius Diamond, Morris Plains, N.J.; George H. Douglas, Paoli, Pa.

[73] Assignee: William H. Rorer, Inc., Fort Washington, Pa.

[21] Appl. No.: 738,426

[22] Filed: Nov. 3, 1976

Related U.S. Application Data

[62] Division of Ser. No. 558,186, Mar. 13, 1975, Pat. No. 4,025,652.

[51] Int. Cl.² .............. A61K 31/33; A61K 31/535; A61K 31/425; A61K 31/445

[52] U.S. Cl. .................... 424/244; 424/246; 424/248.5; 424/248.54; 424/249; 424/250; 424/251; 424/267; 424/269; 424/270; 424/272; 424/273 R; 424/274; 424/273 P

[58] Field of Search ............... 424/248.54, 248.5, 250, 424/251, 244, 246, 274, 267, 270, 249, 269, 272, 273

[56] References Cited

U.S. PATENT DOCUMENTS 3,784,582  1/1974  Walls .................................. 424/322

Primary Examiner—Frederick E. Waddell
Attorney, Agent, or Firm—James A. Nicholson; John C. Smith, Jr.

[57] ABSTRACT

A new class of chemical compounds and their process of preparation is described. These compounds have valuable properties as anti-diarrheal agents.

12 Claims, No Drawings

TREATMENT OF DIARRHEA WITH AMIDINOUREAS

CROSS REFERENCE TO RELATED APPLICATIONS

This is a division of application Ser. No. 558,186 filed Mar. 13, 1975, now U.S. Pat. No. 4,025,652.

SUMMARY OF THE INVENTION

This invention describes a new method for the treatment of diarrhea disorders. This invention further provides valuable pharmaceutical preparations which are effective for the treatment of diarrhea disorders. This invention describes a class of chemical compounds called amidinoureas and the same possess an effective degree of activity which is capable of producing antidiarrhea properties in mammals.

BACKGROUND OF THE INVENTION

Diarrhea is widespread among the world's population. In certain diseases, this enteric disorder can be the cause of a high degree of morbidity and even mortality.

The narcotic analgesics remain the drugs of choice for treatment of diarrhea and dysentery. This group of drugs, however, has serious disadvantages. They possess the narcotic properties of producing sleep as well as analgesia. They also have physical and psychological dependence liabilities. Morphine and codeine remain two outstanding examples of this group.

In 1957 a meperidine derivative, diphenoxylate, was introduced into therapeutic regimen of diarrhea control. This agent possesses morphine-like as well as anticholinergic properties, both of which may be responsible for its anti-diarrheal actions. Diphenoxylate, because of its narcotic properties, is capable of supporting morphine physical dependence in the monkey. Overdoses in children can lead to symptoms and fatalities that are characteristic of the narcotics, e.g. respiratory depression and reversal of morbidity with nalorphine.

Past attempts have failed to indicate that a chemical could be found that would have anti-diarrheal properties without addiction liability, however:

We have unexpectedly found potent anti-diarrheal agents;

We have unexpectedly found a class of chemical compounds which have anti-diarrheal properties without accompanying the effects which are common with these agents;

We have further unexpectedly found that amidinourea compounds are effective antidiarrheal agents having a minimum of side effects;

We have also unexpectedly found that administration of amidinoureas is a simple and effective method for the treatment of diarrhea disorders which does not have physical dependence capacity;

We have still further found effective anti-diarrheal compositions void of undesirable side effects and which have an amidinourea compound as the active ingredient.

DESCRIPTION AND PREFERRED EMBODIMENTS

This invention describes a novel class of chemical compounds of the formula

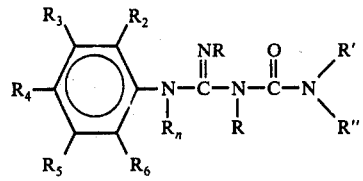

where:

$R_2$, $R_3$, $R_4$, $R_5$ and $R_6$ may be the same or different and are: hydrogen, halo, loweralkyl, haloloweralkyl, nitro, loweralkoxy, hydroxy, arloweralkoxy, acyloxy, cyano, haloloweralkoxy or loweralkylsulfonyl;

R is hydrogen or loweralkyl;

R' and R" are hydrogen, alkyl, cycloalkyl or aralkyl;

R' and R" together and may form a 5–7 atom ring which may include 0–2 hetero atoms of N, O or S;

$R_n$ is hydrogen or loweralkyl provided at least one of R, R' and R" is other than hydrogen; and the non-toxic acid addition salts thereof.

Compounds of this invention which are preferred include those where:

$R_2$, $R_3$, $R_4$, $R_5$ and $R_6$ are hydrogen, halo, loweralkyl, haloloweralkyl, nitro, loweralkoxy or hydroxy;

R and $R_n$ are hydrogen or loweralkyl; and

R' and R" are hydrogen or alkyl; provided R, R' and R" are not all hydrogen at the same time.

The more preferred compounds of this invention include those where:

$R_2$, $R_3$, $R_4$, $R_5$ and $R_6$ are hydrogen, chloro, bromo, fluoro, methyl, ethyl, trifluoromethyl, nitro, methoxy or hydroxy;

R and $R_n$ are hydrogen or loweralkyl; and

R' and R" are hydrogen or alkyl; provided R, R' and R" are not all hydrogen at the same time.

The most preferred compounds of this invention are those where the ortho-positions, that is, the $R_2$ and $R_6$ positions, have electropositive groups such as loweralkyl or loweralkoxy groups present; the meta- and para-positions, that is the $R_3$, $R_4$ and $R_5$ positions have groups such as halo or haloloweralkyl, loweralkoxy or hydroxy.

A special embodiment of this invention comprises compounds useful as anti-diarrheal agents and which have:

$R_3$-halo substitution; $R_4$-halo substitution;

$R_3$, $R_4$ and/or $R_3$, $R_4$ and $R_5$ alkoxy or hydroxy sustitution;

$R_3$, $R_4$-dihalo substitution.

$R_2$, $R_6$-diloweralkyl substitution or $R_2$, $R_6$-loweralkyl, alkoxy substitution.

A further special embodiment of this invention comprises compounds which have:

R, R' and R" as hydrogen or loweralkyl substitution provided all are not hydrogen at the same time; or R and R' are hydrogen or loweralkyl and R" is an alkyl group from 3-carbon atoms.

This invention further describes a novel method for the treatment of diarrhea by the administration of a compound of the formula:

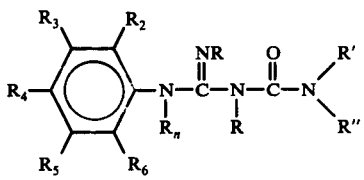

where:
R$_2$, R$_3$, R$_4$, R$_5$ and R$_6$ may be the same or different and are: hydrogen, halo, loweralkyl, naloloweralkyl, nitro, loweralkoxy, hydroxy, arloweralkoxy, acyloxy, cyano, haloloweralkoxy or loweralkylsulfonyl;

R and R$_n$ are hydrogen or loweralkyl;

R' and R" are hydrogen, alkyl, cycloalkyl or aralkyl;

R' and R" together and may form a 5-7 atom ring which may include 0-2 hetero atoms of N, O or S; and the non-toxic acid addition salts thereof.

It is well known in the pharmacological arts that non-toxic acid addition salts of pharmacologically active amine compounds do not differ in activities from their free base. The salts merely provide a convenient solubility factor.

The amines of this invention may be readily converted to their non-toxic acid addition salts by customary methods in the art. The non-toxic salts of this invention are those salts the acid component of which is pharmacologically acceptable in the intended dosages; such salts would include those prepared from inorgnaic acids, organic acids, higher fatty acids, high molecular weight acids, etc., and include such as:

hydrochloric acid,
hyrobromic acid,
sulfuric acid,
nitric acid,
phosphoric acid,
methane sulfonic acid,
benzene sulfonic acid,
acetic acid,
propionic acid,
malic acid,
succinic acid,
glycolic acid,
lactic acid,
salicylic acid,
benzoic acid,
nicotinic acid,
phthalic acid,
stearic acid,
oleic acid,
abietic acid, etc.

The nomenclature applied to the compounds of this invention is as follows:

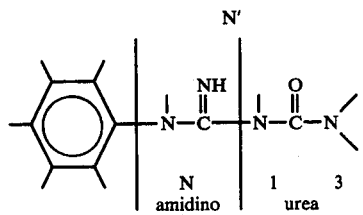

The term loweralkyl refers to an alkyl hydrocarbon group from 1 to 5 carbon atoms which may be straight chained or branched while "alkyl" refers to an alkyl hydrocarbon group which may have as many as ten carbon atoms.

The term "cycloalkyl" refers to a cycloalkyl group having from 3-7 carbon atoms in the ring.

The "loweralkoxy" radical signifies an alkoxy group containing from 1 to about 5 carbon atoms which may be straight chained or branched.

The preferred "aryl" group is phenyl.

The preferred "aralkyl" groups are benzyl and phenethyl.

The preferred "haloloweralkyl" group is trifluoromethyl.

The preferred "haloloweralkoxy" group is trifluoromethoxy.

The compounds of this invention may be prepared by the following general synthesis:

Condensation of cyanamide and a substituted aniline results in the corresponding substituted phenylguanidine.

The reaction is preferably carried out on the aniline salt either in a polar medium or heat and using increased temperatures. The salt used may be any acid addition amine salt but preferably the salt of a mineral acid. The polar medium may be aqueous, partially aqueous or a non-aqueous solution. It is convenient to choose a solvent that will reflux at the desired reaction temperature. The more preferred solvents are water or alcohol but other solvents may be used such as DMSO, diethyleneglycol, ethyleneglycol, tetrahydrofuran, dimethylformamide, etc. The most preferred solvent is a mildly acidic solvent which is non-nucleophilic such as phenol, cresol, xylenol, etc. The reaction should also be carried out at a temperature which is high enough so that condensation takes place readily, but not sufficient to decompose the guanidine formed. The reaction temperature can vary from room temperature to about 250° C although it is preferable to run the reaction at temperatures from about 50° C to 150° C. The guanidine salt which is formed can be converted to the free base with a metal hydroxide or alkoxide solution. The isolation of the desired guanidine can be carried out by any method known in the art.

When the substituted phenylguanidine is reacted with a substituted isocyanate of the formula R'NCO, then the product formed is a 1-substituted phenylamidino-3-R' urea. This reaction is preferably carried out in a nonpolar medium using solvents such as benzene, toluene, xylene, etc. The reaction is also carried out as above at raised temperatures.

The following reaction equations illustrate this synthesis:

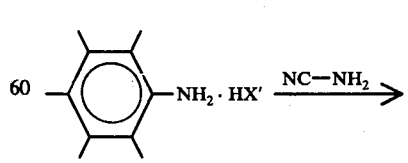

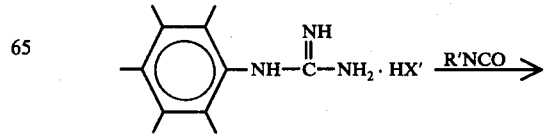

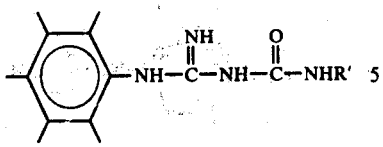

where:

HX' is a mineral acid and R' is other than hydrogen.

When R substitution is desired in the N-position, it is convenient to carry out the condensation using the appropriately N-substituted aniline. Thus, for example, N-methyl-2,6-methylaniline would result in the 1-(2,6-dimethylphenyl)-1-methylguanidine. This is then reacted as above with the isocyanate to form the amidinourea.

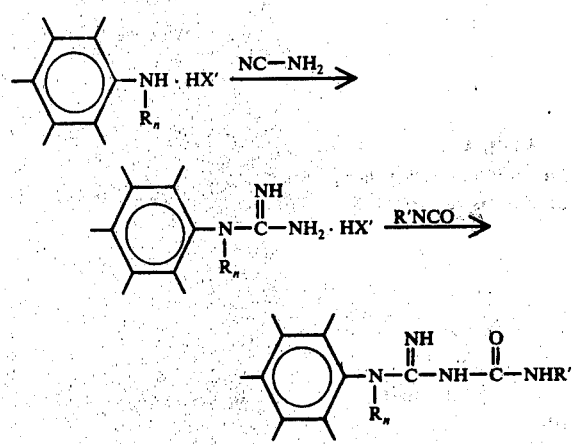

It is convenient to use t-butylisocyanate in the above reaction when R is not desired in the 1-position. This may then be selectively hydrolyzed off.

When R substitution is desired in the 1-position, it is convenient to carry out the condensation using the appropriately substituted cyanamide of the formula NCNHR. Thus, for example, methylcyanamide condensed with 2,6-dimethylaniline would result in the corresponding 1-(2,6-dimethylphenyl)-3-methylguanidine. This is then reacted as above with the isocyanate to form the amidinoureas.

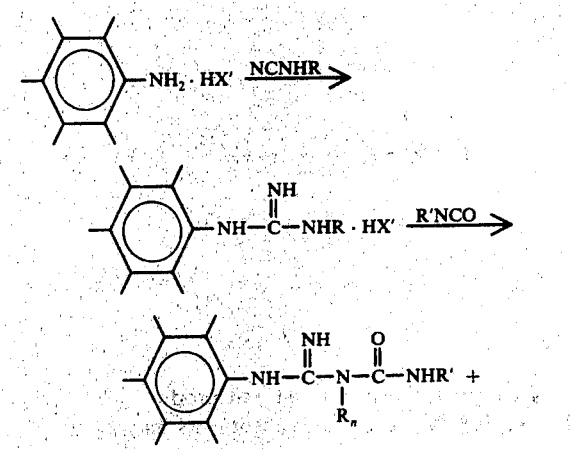

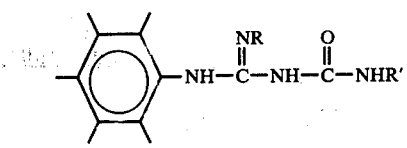

Condensation of an aniline with benzoylthiourea results in the 1-substitutedphenyl-3-benzoylthiourea. This may then be hydrolyzed to the 1-substitutedphenylthiourea and treated with iodomethane to obtain the 1-substitutedphenyl-2-methyl-pseudothiouronium iodide. When the latter is treated with an amine of the formula NH$_2$R$_1$, the resultant displacement yields a 1-substitutedphenyl-3-R guanidine which may then be reacted as above to form the amidinourea.

NH$_4$SCN + φCOCl ⟶ φ—CONCS

φ—CONCS + ⌬—NH$_2$ ⟶

⌬—NH—C(=S)—NHCOφ  $\xrightarrow{10\% NaOH}$

⌬—NH—C(=S)—NH$_2$  $\xrightarrow{CH_3I}$

⌬—NH—C(S—Me)=⊕NH$_2$  I⊖  $\xrightarrow{NHR_3}$

⌬—NH—C(=NH)—NHR  $\xrightarrow{R'NCO}$

⌬—NH—C(=NH)—N(R$_n$)—C(=O)—NHR'

These compounds may also be prepared by condensing the desired aniline with a substituted isothiourea or with a thiocyanate of the formula SCNR. The latter reaction product is the thiourea which is then treated with iodomethane and reacted with an amine of the formula NH$_2$R to obtain the desired guanidine. The above guanidine compounds are reacted with a isocyanate as above to obtain the amidinourea.

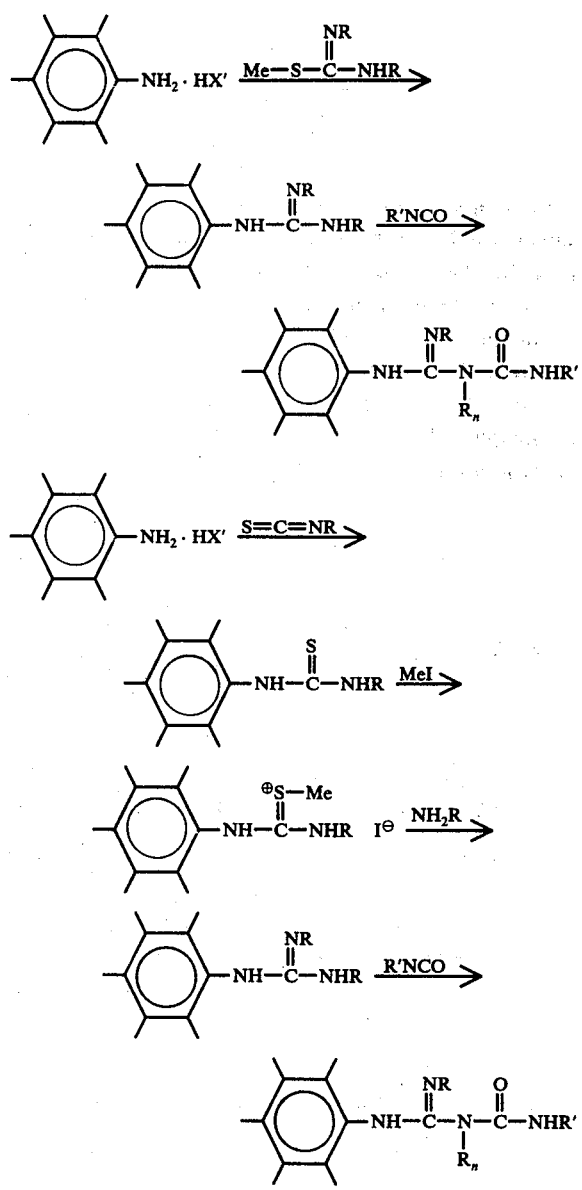

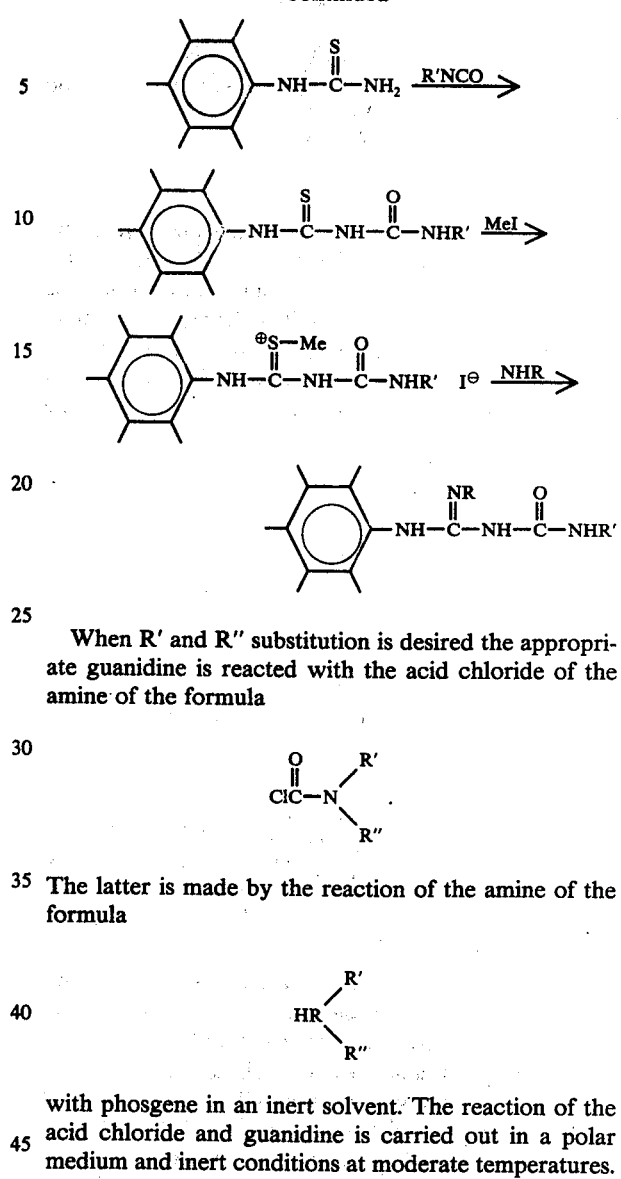

When R substitution is desired in the N'-position, the aniline is condensed with t-butyl thiocyanate of the formula SCN-t-butyl to form the thiourea. The t-butyl group is then hydrolyzed off with conc. HCl. The product is reacted with an isocyanate to obtain the carbamylthiourea, which is treated with iodomethane and reacted with an amine of the formula NHR to obtain the desired amidinourea.

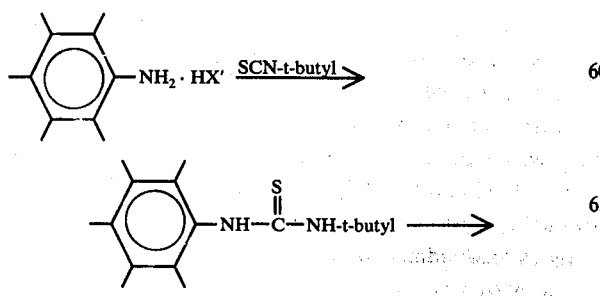

When R' and R'' substitution is desired the appropriate guanidine is reacted with the acid chloride of the amine of the formula $$ClC(=O)-N\begin{matrix}R'\\R''\end{matrix}$$

The latter is made by the reaction of the amine of the formula $$HR-N\begin{matrix}R'\\R''\end{matrix}$$

with phosgene in an inert solvent. The reaction of the acid chloride and guanidine is carried out in a polar medium and inert conditions at moderate temperatures.

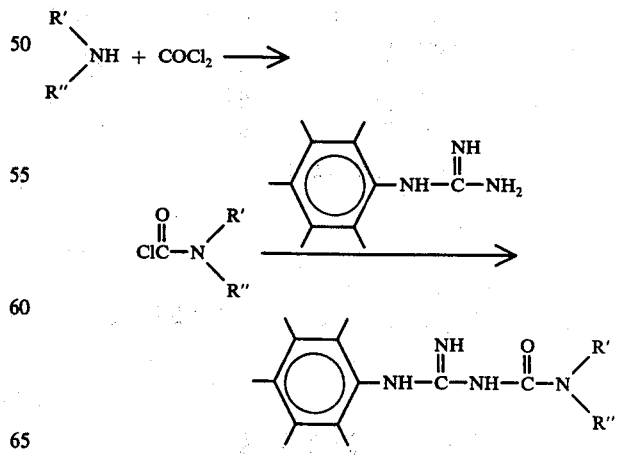

Appropriately desired end products having various $R_2$, $R_3$, $R_4$, $R_5$ and $R_6$ substituents may be prepared at various steps of synthesis using suitable reactions in order to convert one group to another.

The starting anilines are either known, may be prepared by known techniques or reference to the preparation is shown. Thus, chlorination or bromination of an acetanilide or aniline may be carried out in acetic acid, or in the presence of a small amount of iodine dissolved in an inert solvent such as carbon tetrachloride. A solution of chlorine or bromine is then added while the temperature is held near 0° C. Iodination may also be carried out by known methods using iodine monochloride (CII).

Alkylation may be carried out on an acetanilide using an alkyl halide and aluminum chloride under Friedel-Crafts conditions to obtain desired alkyl substitution.

Nitration may be carried out using fuming nitric acid at about 0° C.

A nitro compound may be hydrogenated to the corresponding amine which may then be diazotized and heated in an alcohol medium to form the alkoxy compound.

An amino compound may also be diazotized to the diazonium fluoroborate which is then thermally decomposed to the fluoro compound. Diazotization followed by a Sandmeyer type reaction may yield the bromo, chloro or iodo compound.

A chloro, bromo or iodo compound may also be reacted with trifluoromethyliodide and copper powder at about 150° C in dimethylformamide to obtain a trifluoromethyl compound [Tetrahedron Letters: 47, 4095 (1959).].

A halo compound may also be reacted with cuprous methanesulfinate in quinoline at about 150° C to obtain a methylsulfonyl compound.

When it is desired that the final product contain an hydroxy group, it is preferred that the starting aniline contain the corresponding acyloxy or aralkyloxy groups. These may be prepared in the usual fashion by acylating the starting hydroxy aniline compound with an acyl halide or anhydride in the presence of a tertiary amine or aralkylating with an aralkyl halide or sulfate. Of course the amine function would be protected in the customary manner. Hydrogenation to the desired hydroxy compound may then take place after the formation of the amidinourea. This may be accomplished with a metal catalyst (Pd/C, Pt etc.) in a polar medium (ethanol, THF, etc.) sodium in liquid ammonia etc. Thus, for example, the 3,4-dihydroxy amidinourea compound may be prepared from the corresponding 3,4-dibenzyloxyaniline. The hydroxy compounds may also be prepared by hydrolysis of the acyl or aralkoxy compounds with acid.

Diazotization of an amino compound followed by addition of cuprous cyanide may result in the desired cyano compound.

Of course the above reaction may also be carried out on acetophenone in order to direct substitution. Formation of an oxime followed by Bechmann Rearrangement results in the acetamide which is then deacylated to the aniline.

Reactions may also be carried out on the substituted anilines which would result in di- and tri- substituted anilines.

Reactions may also be carried out at other stages of synthesis depending on the substituents present and the substituents desired and various combinations of the foregoing reactions will be determined by one skilled in the art in order that the desired product results. Thus, a phenylguanidine or amidinourea may be halogenated or nitrated as above, etc.

The compounds described in this application are useful anti-diarrheal agents. For these purposes they can be administered orally, parenterally or rectally. Administration by the oral route is preferred. Orally, these compounds may be administered in tablets, hard or soft capsules, aqueous or oily suspensions, dispersible powders or granules, emulsions, syrups or elixers. The optimum dosage, of course, will depend on the particular compound being used and the type and severity of the condition being treated. In any specific case the appropriate dosage selected will further depend on factors of the patient which may influence response to the drug; for example, general health, age, weight, etc. of the subject being treated.

Although the optimum quantities of the compounds of this invention to be used as anti-diarrheal agents will depend on the compound employed and the particular type of disease condition treated, oral dose levels of preferred compounds when administered to a mammal in dosages of 0.01 to 500 milligrams per kilogram of body weight per day are particularly useful. The preferred range is 0.05 to 200 mg/kg. Comparative dosages may be used in parenteral or rectal administration.

Compositions intended for oral use may be prepared according to methods known to the art for the manufacture of pharmaceutical compositions. Such compositions may contain one or more agents selected from the group consisting of sweetening agents, flavoring agents, coloring agents, preserving agents, etc. in order to provide a pharmaceutically elegant and palatable preparation.

Further the active amidinourea may be administered alone or in admixture with other agents having the same or different pharmacological properties.

The composition may contain such selected excipients such as inert diluents such as calcium carbonate, lactose, etc.; granulating and disintegrating agents such as maize starch, alginic acid, etc.; lubricating agents such as magnesium stearate, etc.; binding agents such as starch gelatin, etc.; suspending agents such as methylcellulose, vegetable oil, etc.; dispersing agents such as lecithin, etc.; thickening agents such as beeswax, hard paraffin, etc.; emulsifying agents such as naturally-occurring gums, etc.; non-irritating excipients such as cocoa butter, polyethylene glycols, etc.; and the like. Further, in formulating these compounds for every 100 parts by weight of the composition, there may be present between 5 and 95 parts by weight of the active ingredient. The dosage unit form will generally contain between 0.5 mg. and about 100 mg. of the active ingredient of this invention. The preferred unit dose is between 1 mg. and about 50 mg. The compositions may be taken 1-8 times daily depending on the dosage unit required.

Various tests can be carried out in animal models to show the ability of the amidinoureas of this invention to exhibit reactions that can be correlated with anti-diarrheal activity in humans. The following tests show the ability of the compounds of this invention to inhibit diarrhea in animals and are known to correlate well with anti-diarrheal activity in humans. These are considered to be standard tests used to determine anti-diarrheal properties. This correlation can be shown by the activities of compounds known to be clinically active. In view of the results of these tests, the amidinoureas of this invention can be considered to be anti-diarrheal agents.

1. Fecal output in rat: - The oral $ED_{50}$ (that dose which would be expected to reduce fecal output by 50%) is determined by a method described by Bass et al., 1972. Briefly, the method involves dosing the rats and collecting the fecal output over an 8 hour period (4PM - 12 midnight) with the room darkened starting at 4:30 P.M.

Ref: - Bass, P., Kennedy, J. A. and Willy, J. N.: Measurement of fecal output in rats. Am. J. Dig. Dis. 10: 925-928, 1972.

2. Castor oil test in mice: - Groups of mice are orally dosed with test compound and half hour later all mice are given 0.3 ml. of castor oil. Three hours after castor oil administration, all mice are checked for diarrhea and the dose of testing compound which protected 50% of mice from diarrhea is the $ED_{50}$ dose.

3. Castor oil test in rats: - The test is conducted according to Niermegeers et al. 1972. The rat is orally dosed with graded doses of test compound. One hour after dosing, each animal is challenged with 1 ml. of castor oil orally. Fecal output is examined 1, 2, 3, 4, 6, and 8 hours after castor oil. Absence of diarrhea is criterion of drug effectiveness.

Ref: - Niemegeers C.J.E., Lenaerts, F. M. and Janssen, P.A.J. Difenoxine, a patent, orally active and safe anti-diarrheal agent in rats. Arzneim-Forscth (Drug Res.) 22, 516–1518, 1972.

EXAMPLE 1

2,6-Dimethylphenylguanidine

To 36 g. (0.315 mole) of 2,6-dimethylaniline is added 0.4 moles of ethereal HCl and 200 ml of m-cresol. The mixture is then stirred and heated on a steam bath to drive off the ether and excess hydrogen chloride. To the resultant mixture is then added 13.3 g. (0.315 mole) of cyanamide then heated for 2 hours on a steam bath. The reaction mixture is then cooled, added to 150 ml. of conc. sodium hydroxide solution, cooled and extracted with 2 liters of ether. The ether layer is washed with 2 × 1 liter of water, dried over sodium sulfate, charcoaled and evaporated. The residue is triturated with hexane and the precipitate is filtered off and washed with ether and dried to obtain 2,6-dimethylphenylguanidine.

When the above procedures are followed using the amines of Table I, below, then the corresponding product of Table II, below, is prepared.

| Table I | Table II |
|---|---|
| m-chloroaniline | m-chlorophenylguanidine |
| p-chloroaniline | p-chlorophenylguanidine |
| 2,3-dichloroaniline | 2,3-dichlorophenylguanidine |
| 3,4-dichloroaniline | 3,4-dichlorophenylguanidine |
| 3,5-dichloroaniline | 3,5-dichlorophenylguanidine |
| 3,4,5-trichloroaniline | 3,4,5-trichlorophenylguanidine |
| m-bromoaniline | m-bromophenylguanidine |
| p-bromoaniline | p-bromophenylguanidine |
| 2,5-dibromoaniline | 2,5-dibromophenylguanidine |
| 3,4-dibromoaniline | 3,4-dibromophenylguanidine |
| 3,5-dibromoaniline | 3,5-dibromophenylguanidine |
| 3-chloro-4-bromoaniline | 3-chloro-4-bromophenylguanidine |
| 3-chloro-5-bromoaniline | 3-chloro-5-bromophenylguanidine |
| 4-chloro-3-bromoaniline | 4-chloro-3-bromophenylguanidine |
| m-fluoroaniline | m-fluorophenylguanidine |
| p-fluoroaniline | p-fluorophenylguuanidine |
| p-iodoaniline | p-iodophenylguanidine |
| 3,4-difluoroaniline | 3,4-difluorophenylguanidine |
| 3,5-difluoroaniline | 3,5-difluorophenylguanidine |
| 3-fluoro-4-chloroaniline | 3-fluoro-4-chlorophenylguanidine |
| 3-fluoro-5-chloroaniline | 3-fluoro-5-chlorophenylguanidine |
| 3-chloro-4-fluoroaniline | 3-chloro-4-fluorophenylguanidine |
| 3-fluoro-4-bromoaniline | 3-fluoro-4-bromophenylguanidine |
| 3-bromo-4-fluoroaniline | 3-bromo-4-fluorophenylguanidine |
| 3-chloro-4-iodoaniline | 3-chloro-4-iodophenylguanidine |
| 3-iodo-4-bromoaniline | 3-iodo-4-bromophenylguanidine |
| 3-iodo-4-chloroaniline | 3-iodo-4-chlorophenylguanidine |
| 3-bromo-4-iodoaniline | 3-bromo-4-iodophenylguanidine |
| 3-fluoro-4-iodoaniline | 3-fluoro-4-iodophenylguanidine |
| 3-iodo-4-fluoroaniline | 3-iodo-4-fluorophenylguanidine |
| 3,4-dimethoxyaniline | 3,4-dimethoxyphenylguanidine |
| 3,4,5-trimethoxyaniline | 3,4,5-trimethoxyphenylguanidine |
| 3,4-diethoxyaniline | 3,4-diethoxyphenylguanidine |
| 3,4,5-triethoxyaniline | 3,4,5-triethoxyphenylguanidine |
| 3-methoxy-4-chloroaniline | 3-methoxy-4-chlorophenylguanidine |
| 3-chloro-4-methoxyaniline | 3-chloro-4-methoxyphenylguanidine |
| m-trifluoromethylaniline | m-trifluoromethylphenylguanidine |
| p-trifluoromethylaniline | p-trifluoromethylphenylguanidine |
| p-trifluoromethoxyaniline | p-trifluoromethoxyphenylguanidine |
| p-methylsulfonylaniline | p-methylsulfonylphenylguanidine |
| p-nitroaniline | p-nitrophenylguanidine |
| 3-chloro-4-nitroaniline | 3-chloro-4-nitrophenylguanidine |
| 3-bromo-4-nitroaniline | 3-bromo-4-nitrophenylguanidine |
| 3-fluoro-4-nitroaniline | 3-fluoro-4-nitrophenylguanidine |
| 3-nitro-4-chloroaniline | 3-nitro-4-chlorophenylguanidine |
| 3-nitro-4-bromoaniline | 3-nitro-4-bromophenylguanidine |
| 3-nitro-4-fluoroaniline | 3-nitro-4-fluorophenylguanidine |
| 3-chloro-4-trifluoromethylaniline | 3-chloro-4-trifluoromethylphenylguanidine |
| 3-bromo-4-trifluoromethylaniline | 3-bromo-4-trifluoromethylphenylguanidine |
| 3-fluoro-4-trifluoromethylaniline | 3-fluoro-4-trifluoromethylphenylguanidine |
| 3-chloro-4-methoxyaniline | 3-chloro-4-methoxyphenylguanidine |
| 3-chloro-4-cyanoaniline | 3-chloro-4-cyanophenylguanidine |
| 2-methyl-3-chloroaniline | 2-methyl-3-chlorophenylguanidine |
| 2-methyl-4-chloroaniline | 2-methyl-4-chlorophenylguanidine |
| 2-methyl-5-chloroaniline | 2-methyl-5-chlorophenylguanidine |
| 2-methyl-3-bromoaniline | 2-methyl-3-bromophenylguanidine |
| 2-methyl-4-bromoaniline | 2-methyl-4-bromophenylguanidine |

-continued

| Table I | Table II |
|---|---|
| 2-methyl-5-bromoaniline | 2-methyl-5-bromophenylguanidine |
| 2-methyl-3-fluoroaniline | 2-methyl-3-fluorophenylguanidine |
| 2-methyl-4-fluoroaniline | 2-methyl-4-fluorophenylguanidine |
| 2-methyl-5-fluoroaniline | 2-methyl-5-fluorophenylguanidine |
| 2-methyl-4-nitroaniline | 2-methyl-4-nitrophenylguanidine |
| 2-methyl-4-cyanoaniline | 2-methyl-4-cyanophenylguanidine |
| 2-methyl-4-trifluoromethylaniline | 2-methyl-4-trifluoromethylphenylguanidine |
| 2-methyl-5-trifluoromethylaniline | 2-methyl-5-trifluoromethylphenylguanidine |
| 2-methyl-6-ethylaniline | 2-methyl-6-ethylphenylguanidine |
| 2-methyl-6-propylaniline | 2-methyl-6-propylphenylguanidine |
| 2,6-diethylaniline | 2,6-diethylphenylguanidine |
| 2-methyl-6-methoxyaniline | 2-methyl-6-methoxyphenylguanidine |
| 2-methyl-6-ethoxyaniline | 2-methyl-6-ethoxyphenylguanidine |
| 2-ethyl-6-methoxyaniline | 2-ethyl-6-methoxyphenylguanidine |
| 2-ethyl-6-ethoxyaniline | 2-ethyl-6-ethoxyphenylguanidine |
| 2-methyl-3,4-dichloroaniline | 2-methyl-3,4-dichlorophenylquanidine |
| 2-methyl-3,5-dichloroaniline | 2-methyl-3,5-dichlorophenylguanidine |
| 2-methyl-3,4,5-trichloroaniline | 2-methyl-3,4,5-trichlorophenylguanidine |
| 2-methyl-3,5-dichloro-4-bromoaniline | 2-methyl-3,5-dichloro-4-bromophenylguanidine |
| 2,6-dimethyl-3-chloroaniline | 2,6-dimethyl-3-chlorophenylguanidine |
| 2,6-dimethyl-4-chloroaniline | 2,6-dimethyl-4-chlorophenylguanidine |
| 2,6-dimethyl-3-fluoroaniline | 2,6-dimethyl-3-fluorophenylguanidine |
| 2,6-dimethyl-4-bromoaniline | 2,6-dimethyl-4-bromophenylguanidine |
| 2,6-diethyl-3-chloroaniline | 2,6-diethyl-3-chlorophenylguanidine |
| 2,6-diethyl-4-chloroaniline | 2,6-diethyl-4-chlorophenylguanidine |
| 2,6-dimethyl-3,4-dichloroaniline | 2,6-dimethyl-3,4-dichlorophenylguanidine |
| 2,6-dimethyl-3,5-dichloroaniline | 2,6-dimethyl-3,5-dichlorophenylguanidine |
| 2,6-dimethyl-3,4,5-trichloroaniline | 2,6-dimethyl-3,4,5-trichlorophenylguanidine |
| 3-trifluoromethyl-4-methylaniline | 3-trifluoro-4-methylphenylguanidine |
| 2,6-dimethyl-4-trifluoromethylaniline | 2,6-dimethyl-4-trifluoromethylphenylguanidine |
| 2-ethyl-4-nitroaniline | 2-ethyl-4-nitrophenylguanidine |
| 2-ethyl-4-chloroaniline | 2-ethyl-4-chlorophenylguanidine |
| 2-ethyl-4-bromoaniline | 2-ethyl-4-bromophenylguanidine |
| 2-ethyl-4-fluoroaniline | 2-ethyl-4-fluorophenylguanidine |
| 2-ethyl-4-trifluoromethylaniline | 2-ethyl-4-trifluoromethylphenylguanidine |
| 2,4-dichloro-6-methylaniline | 2,4-dichloro-6-methylphenylguanidine |
| 2,6-dichloro-4-methylaniline | 2,6-dichloro-4-methylphenylguanidine |
| 2,4-dibromo-6-methylaniline | 2,4-dibromo-6-methylphenylguanidine |
| 2,6-dibromo-4-methylaniline | 2,6-dibromo-4-methylphenylguanidine |
| 2-chloro-4-methyl-6-fluoroaniline | 2-chloro-4-methyl-6-fluorophenylguanidine |
| 2,4-dimethyl-6-chloroaniline | 2,4-dimethyl-6-chlorophenylguanidine |
| 2,4-dimethyl-6-fluoroaniline | 2,4-dimethyl-6-fluorophenylguanidine |
| 2-chloro-4-fluoro-6-methylaniline | 2-chloro-4-fluoro-6-methylphenylguanidine |
| 3,4-dibenzyloxyaniline | 3,4-dibenzyloxyphenylguanidine |
| 3,4,5-tribenzyloxyaniline | 3,4,5-tribenzyloxyphenylguanidine |

EXAMPLE 2

1-(2,6-dimethylphenyl)-1-methylguanidine

To 40.5 g. (0.315 mole) of N-methyl-2,6-dimethylaniline is added 0.4 moles of ethereal HCl and 200 ml. of m-cresol. The mixture is then stirred and heated on a steam bath to drive off the ether and excess hydrogen chloride. To the resultant mixture is then added 13.3 g. (0.315 mole) of cyanamide then heated for 2 hours on a steam bath. The reaction mixture is then cooled, added to 150 ml. of conc. sodium hydroxide solution, cooled and extracted with 2 liters of ether. The ether layer is washed with 2 × 1 liter of water, dried over sodium sulfate, charcoaled and evaporated. The residue is triturated with hexane and the precipitate is filtered off and washed with ether and dried to obtain 1-(2,6-dimethylphenyl)-1-methylguanidine.

When the N-methylaniline in the above procedures is replaced by the N-loweralkylanilines of this invention then the corresponding product is obtained.

When the above procedures are followed using the representative amines of Table I, below, then the corresponding product of Table II, below, is prepared.

| Table I | Table II |
|---|---|
| N-methyl-m-chloroaniline | 1-(m-chlorophenyl)-1-methylguanidine |
| N-methyl-p-chloroaniline | 1-(p-chlorophenyl)-1-methylguanidine |
| N-methyl-3,4-dichloroaniline | 1-(3,4-dichlorophenyl)-1-methylguanidine |
| N-methyl-3,5-dichloroaniline | 1-(3,5-dichlorophenyl)-1-methylguanidine |
| N-methyl-3,4,5-trichloroaniline | 1-(3,4,5-trichlorophenyl)-1-methylguanidine |
| N-methyl-m-bromoaniline | 1-(m-bromophenyl)-1-methylguanidine |
| N-methyl-p-bromoaniline | 1-(p-bromophenyl)-1-methylguanidine |
| N-methyl-3,4-dibromoaniline | 1-(3,4-dibromophenyl)-1-methylguanidine |
| N-methyl-3-chloro-4-bromoaniline | 1-(3-chloro-4-bromophenyl)-1-methylguanidine |
| N-methyl-3-chloro-5-bromoaniline | 1-(3-chloro-5-bromophenyl)-1-methylguanidine |
| N-methyl-4-chloro-3-bromoaniline | 1-(4-chloro-3-bromophenyl)-1-methylguanidine |
| N-methyl-3-chloro-4-fluoroaniline | 1-(3-chloro-4-fluorophenyl)-1-methylguanidine |
| N-methyl-3-chloro-4-iodoaniline | 1-(3-chloro-4-iodophenyl)-1-methylguanidine |
| N-methyl-m-fluoroaniline | 1-(m-fluorophenyl)-1-methylguanidine |
| N-methyl-p-fluoroaniline | 1-(p-fluorophenyl)-1-methylguanidine |
| N-methyl-p-iodoaniline | 1-(p-iodophenyl)-1-methylguanidine |
| N-methyl-3,4-dimethoxyaniline | 1-(3,4-dimethoxyphenyl)-1-methylguanidine |
| N-methyl-3,4,5-trimethoxyaniline | 1-(3,4,5-trimethoxyphenyl)-1-methylguanidine |
| N-methyl-3,4-difluoroaniline | 1-(3,4-difluorophenyl)-1-methylguanidine |
| N-methyl-3,5-difluoroaniline | 1-(3,5-difluorophenyl)-1-methylguanidine |
| N-methyl-m-trifluoromethylaniline | 1-(m-trifluoromethylphenyl)-1-methylguanidine |

| Table I -continued | Table II |
|---|---|
| N-methyl-m-trifluoromethylaniline | 1-(m-trifluoromethylphenyl)-1-methylguanidine |
| N-methyl-p-trifluoromethylaniline | 1-(p-trifluoromethylphenyl)-1-methylguanidine |
| N-methyl-p-trifluoromethoxyaniline | 1-(p-trifluoromethoxyphenyl)-1-methylguanidine |
| N-methyl-p-methylsulfonylaniline | 1-(p-methylsulfonylphenyl)-1-methylguanidine |
| N-methyl-p-nitroaniline | 1-(p-nitrophenyl)-1-methylguanidine |
| N-methyl-2-methyl-4-chloroaniline | 1-(2-methyl-4-chlorophenyl)-1-methylguanidine |
| N-methyl-2-methyl-4-bromoaniline | 1-(2-methyl-4-bromophenyl)-1-methylguanidine |
| N-methyl-2-chloro-4-methylaniline | 1-(2-chloro-4-methylphenyl)-1-methylguanidine |
| N-methyl-2-methyl-4-nitroaniline | 1-(2-methyl-4-nitrophenyl)-1-methylguanidine |
| N-methyl-2-methyl-4-trifluoromethyl aniline | 1-(2-methyl-4-trifluoromethylphenyl)-1-methylguanidine |
| N-methyl-2-methyl-6-chloroaniline | 1-(2-methyl-6-chlorophenyl)-1-methylguanidine |
| N-methyl-2,4-dimethylaniline | 1-(2,4-dimethylphenyl)-1-methylguanidine |
| N-methyl-2,6-dimethylaniline | 1-(2,6-dimethylphenyl)-1-methylguanidine |
| N-methyl-3,5-ditrifluoromethyl-aniline | 1-(3,5-ditrifluoromethylphenyl)-1-methyl-guanidine |
| N-methyl-2,6-dimethyl-4-chloro-aniline | 1-(2,6-dimethyl-4-chlorophenyl)-1-methyl guanidine |
| N-methyl-2,6-dimethyl-4-fluoro-aniline | 1-(2,6-dimethyl-4-fluorophenyl)-1-methyl-guanidine |
| N-methyl-2,6-dimethyl-4-bromo-aniline | 1-(2,6-dimethyl-4-bromophenyl)-1-methyl-guanidine |
| N-methyl-2,6-dimethyl-4-trifluoromethyl-aniline | 1-(2,6-dimethyl-4-trifluoromethylphenyl)-1-methylguanidine |
| N-methyl-2-ethyl-4-chloroaniline | 1-(2-ethyl-4-chlorophenyl)-1-methylguanidine |
| N-methyl-2-ethyl-4-bromoaniline | 1-(2-ethyl-4-bromophenyl)-1-methylguanidine |
| N-methyl-2-ethyl-4-fluoroaniline | 1-(2-ethyl-4-fluorophenyl)-1-methylguanidine |
| N-methyl-2-ethyl-4-trifluoromethyl-aniline | 1-(2-ethyl-4-trifluoromethylphenyl)-1-methylguanidine |
| N-methyl-2,6-dimethyl-4-bromoaniline | 1-(2,6-dimethyl-4-bromophenyl)-1-methyl-guanidine |
| N-methyl-2,6-dimethyl-4-chloro-aniline | 1-(2,6-dimethyl-4-chlorophenyl)-1-methylguanidine |
| N-methyl-2,6-dimethyl-4-fluoro-aniline | 1-(2,6-dimethyl-4-fluorophenyl)-1-methylguanidine |
| N-ethyl-p-fluoroaniline | 1-(p-fluorophenyl)-1-ethylguanidine |
| N-propyl-p-fluoroaniline | 1-(p-fluorophenyl)-1-propylguanidine |
| 5-N-methyl-3,4-dibenzyloxyaniline | 1-(3,4-dibenzyloxyphenyl)-1-methylguanidine |
| N-methyl-3,4,5-tribenzyloxy-aniline | 1-(3,4,5-tribenzyloxyphenyl)-1-methylguanidine |
| N-ethyl-2,6-dimethylaniline | 1-(2,6-dimethylphenyl)-1-ethylguanidine |
| N-methyl-2-ethyl-6-methylaniline | 1-(2-ethyl-6-methylphenyl)-1-methylguanidine |

EXAMPLE 3

1-(2,6-dimethylphenyl)-3-methylguanidine

To 40.5 g. (0.315 mole) of 2,6-dimethylaniline is added 0.4 moles of ethereal HCl and 200 ml. of m-cresol. The mixture is then stirred and heated on a steam bath to drive off the ether and excess hydrogen chloride. To the resultant mixture is then added 17.7 g. (0.315 mole) of methyl cyanamide then heated for 2 hours on a steam bath. The reaction mixture is then cooled, added to 150 ml. of conc. sodium hydroxide solution, cooled and extracted with 2 liters of ether. The ether layer is washed with 2 × 1 liter of water, dried over sodium sulfate, charcoaled and evaporated. The residue is triturated with hexane and the precipitate is filtered off and washed with ether and dried to obtain 1-(2,6-dimethylphenyl)-3-methylguanidine.

When the above procedures are followed using the cyanamides of Table I below, then the corresponding products are prepared.

Table I
ethylcyanamide
propylcyanamide
i-propylcyanamide
butylcyanamide
pentylcyanamide When the anilines of Examples 1 and 2 are condensed with the above cyanamides using the above procedures, then the corresponding products are obtained.

EXAMPLE 4

1-(p-fluorophenyl)-3-methylthiourea

To a mixture of 55.5 g. (0.5 mole) of p-fluoroaniline and 100 ml. of xylene is added 36.5 g. (0.5 mole) of methylisothiocyanate and the mixture is refluxed for 2 hours. The reaction product is cooled, triturated with heptane and filtered. Recrystallization from 1:1 isopropanol/water results in 1-(p-fluorophenyl)-3-methylthiourea.

When the above procedure is followed using 2,6-dimethylaniline then the product prepared is 1-(2,6-dimethylphenyl)-3-methylthiourea.

When the above procedure is followed using the anilines of Example 1 and 2 then the corresonding product is obtained.

When methylisothiocyanate is replaced by the isothiocyanates of Table I below, then the corresponding product is obtained.

Table I
ethylisothiocyanate
propylisothiocyanate
i-propylisothiocyanate
butylisothiocyante
pentylisothiocyanate
hexylisothiocyanate

EXAMPLE 5

1-(2,6-dimethylphenyl)-3-methylguanidine 1-(2,6-dimethylphenyl)-3-benzoylthiourea To 51.0 g. (0.68 mole) of ammonium thiocyanate in 300 ml. acetone is added 86.8 g. (0.62 mole) of benzoyl chloride. The reaction mixture is refluxed for about 5 min. and then 81 g. (0.62 mole) of 2,6-dimethylaniline in 200 ml. acetone is added at a rate to maintain reflux. The mixture is refluxed for 1-1/2 hours, cooled, poured into 1-1/2 liters of ice and water, filtered to obtain 1-(2,6-dimethylphenyl)-3-benzoylthiourea.

2,6-dimethylphenylthiourea 182.8 g. (0.56 mole) of 1-(2,6-dimethylphenyl)-3-benzoylthiourea is heated with 260 ml. of 10% sodium hydroxide, filtered, acidified while hot with conc. hydrochloric acid and then made basic with conc. ammonium hydroxide. The mixture is then chilled in an ice bath and the resultant 2,6-dimethylphenylthiourea is filtered off.

1-(2,6-dimethylphenyl)-2-methylpseudothiouronium iodide 16 g. (0.09 mole) of 2,6-dimethylphenylthiourea is combined with 200 ml. methanol and 12.9 g. (0.09 mole) iodomethane and refluxed for 4 hours. This is then evaporated to dryness and 100 ml. hexane is added and the mixture filtered to obtain 1-(2,6-dimethylphenyl)-2-methylpseudothiouronium iodide.

1-(2,6-dimethylphenyl)-3-methylguanidine hydrochloride 26.2 g. (0.09 mole) of 1-(2,6-dimethylphenyl)-2-methylpseudothiouronium iodide is added to 300 ml. of n-butanol. Methylamine gas is bubbled through this solution while refluxing for 24 hours. The reaction mixture is evaporated to dryness and extracted with 10% sodium hydroxide solution and ether. The ether is washed with 10% sodium hydroxide and then with water, dried and filtered. To this is added ethereal HCl and the precipitate is collected to obtain 1-(2,6-dimethylphenyl)-3-methylguanidine hydrochloride.

The free base is prepared by dissolving 1-(2,6-dimethylphenyl)-3-methylguanidine hydrochloride in 10% sodium hydroxide solution and extracting with ether. The ether is dried and evaporated to dryness to obtain 1-(2,6-dimethylphenyl)-3-methylguanidine.

When the above procedures are followed using the anilines of Examples 1 and 2, then the corresponding product is obtained.

When the above procedures are followed and methylamine is replaced with the amines of Table I below, then the corresonding product is obtained.

Table I

| |
|---|
| ethylamine |
| propylamine |
| i-propylamine |
| butylamine |
| pentylamine |

When the above procedures are followed using the anilines of Examples 1 and 2 and the amines of Table I above the corresonding products are obtained.

When the thiourea compunds prepared of Example 4 are substituted in the above procedure, then the corresonding products are obtained.

EXAMPLE 6

1-(2,6-dimethylphenylamidino)-3-(t-butyl)urea

To a mixture of 8 g. (0.05 mole) of 2,6-dimethylphenylguanidine and 10 ml. xylene is added dropwise 5 g. of t-butylisocyanate (0.05 mole) and the mixture is refluxed for 2 hours. The reaction product is cooled, triturated with heptane and filtered. Recrystallization from 1:1 isopropanol/water results in 1-(2,6-dimethylphenylamidino)-3-(t-butyl)urea.

When the above precedure is followed using the guanidines of Example 1, then the corresponding products are prepared.

Table I 1-(m-chlorophenylamidino)-3-(t-butyl)urea
1-(p-chlorophenylamidino)-3-(t-butyl)urea
1-(2,3-dichlorophenylamidino)-3-(t-butyl)urea
1-(3,4-dichlorophenylamidino)-3-(t-butyl)urea
1-(3,5-dichlorophenylamidino)-3-(t-butyl)urea
1-(3,4,5-trichlorophenylamidino)-3-(t-butyl)urea
1-(m-bromophenylamidino)-3-(t-butyl)urea
1-(p-bromophenylamidino)-3-(t-butyl)urea
1-(2,5-dibromophenylamidino)-3-(t-butyl)urea
1-(3,4-dibromophenylamidino)-3-(t-butyl)urea
1-(3,5-dibromophenylamidino)-3-(t-butyl)urea
1-(3-chloro-4-bromophenylamidino)-3-(t-butyl)urea
1-(3-chloro-5-bromophenylamidino)-3-(t-butyl)urea
1-(4-chloro-3-bromophenylamidino)-3-(t-butyl)urea
1-(m-fluorophenylamidino)-3-(t-butyl)urea
1-(p-fluorophenylamidino)-3-(t-butyl)urea
1-(p-iodophenylamidino)-3-(t-butyl)urea
1-(3,4-difluorophenylamidino)-3-(t-butyl)urea
1-(3,5-difluorophenylamidino)-3-(t-butyl)urea
1-(3-fluoro-4-chlorophenylamidino)-3-(t-butyl)urea
1-(3-fluoro-5-chlorophenylamidino)-3-(t-butyl)urea
1-(3-chloro-4-fluorophenylamidino)-3-(t-butyl)urea
1-(3-fluoro-4-bromophenylamidino)-3-(t-butyl)urea
1-(3-bromo-4-fluorophenylamidino)-3-(t-butyl)urea
1-(3-chloro-4-iodophenylamidino)-3-(t-butyl)urea
1-(3-iodo-4-bromophenylamidino)-3-(t-butyl)urea
1-(3-iodo-4-chlorophenylamidino)-3-(t-butyl)urea
1-(3-bromo-4-iodophenylamidino)-3-(t-butyl)urea
1-(3-fluoro-4-iodophenylamidino)-3-(t-butyl)urea
1-(3-iodo-4-fluorophenylamidino)-3-(t-butyl)urea
1-(3,4-dimethoxyphenylamidino-3-(t-butyl)urea
1-(3,4,5-trimethoxyphenylamidino)-3-(t-butyl)urea
1-(3,4-diethoxyphenylamidino)-3-(t-butyl)urea
1-(3,4,5-triethoxyphenylamidino)-3-(t-butyl)urea
1-(3-methoxy-4-chlorophenylamidino)-3-(t-butyl)urea
1-(3-chloro-4-methoxyphenylamidino)-3-(t-butyl)urea
1-(m-trifluoromethylphenylamidino)-3-(t-butyl)urea
1-(p-trifluoromethylphenylamidino)-3-(t-butyl)urea
1-(p-trifluoromethoxyphenylamidino)-3-(t-butyl)urea
1-(p-methylsulfonylphenylamidino)-3-(t-butyl)urea
1-(p-nitrophenylamidino)-3-(t-butyl)urea
1-(3-chloro-4-nitrophenylamidino)-3-(t-butyl)urea
1-(3-bromo-4-nitrophenylamidino)-3-(t-butyl)urea
1-(3-fluoro-4-nitrophenylamidino)-3-(t-butyl)urea
1-(3-nitro-4-chlorophenylamidino)-3-(t-butyl)urea
1-(3-nitro-4-bromophenylamidino)-3-(t-butyl)urea
1-(3-nitro-4-fluorophenylamidino)-3-(t-butyl)urea
1-(3-chloro-4-trifluoromethylphenylamidino)-3-(t-butyl)urea
1-(3-bromo-4-trifluoromethylphenylamidino)-3-(t-butyl)urea
1-(3-fluoro-4-trifluoromethylphenylamidino)-3-(t-butyl)urea
1-(3-chloro-4-methoxyphenylamidino)-3-(t-butyl)urea
1-(3-chloro-4-cyanophenylamidino)-3-(t-butyl)urea
1-(2-methyl-3-chlorophenylamidino)-3-(t-butyl)urea
1-(2-methyl-4-chlorophenylamidino)-3-(t-butyl)urea
1-(2-methyl-5-chlorophenylamidino)-3-(t-butyl)urea
1-(2-methyl-3-bromophenylamidino)-3-(t-butyl)urea
1-(2-methyl-4-bromophenylamidino)-3-(t-butyl)urea
1-(2-methyl-5-bromophenylamidino)-3-(t-butyl)urea
1-(2-methyl-3-fluorophenylamidino)-3-(t-butyl)urea
1-(2-methyl-4-fluorophenylamidino)-3-(t-butyl)urea
1-(2-methyl-5-fluorophenylamidino)-3-(t-butyl)urea
1-(2-methyl-4-nitrophenylamidino)-3-(t-butyl)urea
1-(2-methyl-4-cyanophenylamidino)-3-(t-butyl)urea
1-(2-methyl-4-trifluoromethylphenylamidino)-3-(t-butyl)urea
1-(2-methyl-5-trifluoromethylphenylamidino)-3-(t-butyl)urea
1-(2-methyl-6-ethylphenylamidino)-3-(t-butyl)urea
1-(2-methyl-6-propylphenylamidino)-3-(t-butyl)urea
1-(2,6-diethylphenylamidino)-3-(t-butyl)urea
1-(2-methyl-6-methoxyphenylamidino)-3-(t-butyl)urea
1-(2-methyl-6-ethoxyphenylamidino)-3-(t-butyl) urea
1-(2-ethyl-6-methoxyphenylamidino)-3-(t-butyl)urea
1-(2-ethyl-6-ethoxyphenylamidino)-3-(t-butyl)urea
1-(2-methyl-3,4-dichlorophenylamidino)-3-(t-butyl)urea
1-(2-methyl-3,5-dichlorophenylamidino)-3-(t-butyl)urea
1-(2-methyl-3,4,5-trichlorophenylamidino)-3-(t-butyl)urea
1-(2-methyl-3,5-dichloro-4-bromophenylamidino)-3-(t-butyl)urea
1-(2,6-dimethyl-4-chlorophenylamidino)-3-(t-butyl)urea
1-(2,6-dimethyl-3-bromophenylamidino)-3-(t-butyl)urea
1-(2,6-dimethyl-3-fluorophenylamidino)-3-(t-butyl)urea
1-(2,6-dimethyl-4-bromophenylamidino)-3-(t-butyl)urea
1-(2,6-dimethyl-4-fluorophenylamidino)-3-(t-butyl)urea
1-(2,6-diethyl-3-chlorophenylamidino)-3-(t-butyl)urea
1-(2,6-diethyl-4-chlorophenylamidino)-3-(t-butyl)urea
1-(2,6-dimethyl-3,4-dichlorophenylamidino)-3-(t-butyl)urea
1-(2,6-dimethyl-3,5-dichlorophenylamidino)-3-(t-butyl)urea
1-(2,6-dimethyl-3,4,5-trichlorophenylamidino)-3-(t-butyl)urea
1-(3-trifluoromethyl-4-methylphenylamidino)-3-(t-butyl)urea
1-(2,6-dimethyl-4-trifluoromethylphenylamidino)-3-(t-butyl)urea
1-(2-ethyl-4-nitrophenylamidino)-3-(t-butyl)urea
1-(2-ethyl-4-chlorophenylamidino)-3-(t-butyl)urea

Table I-continued 1-(2-ethyl-4-bromophenylamidino)-3-(t-butyl)urea
1-(2-ethyl-4-fluorophenylamidino)-3-(t-butyl)urea
1-(2-ethyl-4-trifluoromethylphenylamidino)-3-(t-butyl)urea
1-(2,4-dichloro-6-methylphenylamidino)-3-(t-butyl)urea
1-(2,6-dichloro-4-methylphenylamidino)-3-(t-butyl)urea
1-(2,4-dibromo-6-methylphenylamidino)-3-(t-butyl)urea
1-(2,6-dibromo-4-methylphenylamidino)-3-(t-butyl)urea
1-(2-chloro-4-methyl-6-fluorophenylamidino)-3-(t-butyl)urea
1-(2,4-dimethyl-6-chlorophenylamidino)-3-(t-butyl)urea
1-(2,4-dimethyl-6-fluorophenylamidino)-3-(t-butyl)urea
1-(2-chloro-4-fluoro-6-methylphenylamidino)-3-(t-butyl)urea
1-(3,4-dibenzyloxyphenylamidino)-3-(t-butyl)urea
1-(3,4,5-tribenzyloxyphenylamino)3-(t-butyl)urea When t-butylisocyanate in the above procedure is replaced by the isocyanates of Table II below, then the corresonding product is prepared.

Table II methylisocyanate
ethylisocyanate
propylisocyanate
i-propylisocyanate
butylisocyanate
pentylisocyanate
cyclopropylisocyanate
cyclobutylisocyanate
cyclopentylisocyanate
cyclohexylisocyanate
phenylisocyanate
benzylisocyanate
phenethylisocyanate When the above procedure is followed using the guanidines of Example 1 and 3 and the isocyanates of Table II above, then the corresponding product is prepared.

EXAMPLE 7

1-(2,6-dimethylphenyl-N-methylamidino)urea 1-(2,6-dimethylphenyl-N-methylamidino)-3-(t-butyl)urea To a mixture of 8.7 g. (0.05 mole) of 1-(2,6-dimethylphenyl)-1-methylguanidine and 10 ml. xylene is added 5 g. of t-butylisocyanate (0.05 mole) and the mixture is refluxed for 2 hours. The reaction product is cooled, triturated with heptane and filtered. Recrystallization from 1:1 isopropanol/water results in 1-(2,6-dimethylphenyl-N-methylamidino)-3-(t-butyl)urea.

1-(2,6-dimethylphenyl-N-methylamidino)urea

A mixture of 27 g. (0.106 mole) of 1-(2,6-dimethylphenyl-N-methylamidino)-3-(t-butyl)urea and 200 ml. of conc. hydrochloric acid is refluxed for ½ hour. The reaction mixture is cooled, the precipitated solid filtered and washed with 10 ml. of 1:1 HCl/H$_2$O and dried. The product is then recrystallized from ethanol-ether to obtain 1-(2,6-dimethylphenyl-N-methylamidino)urea.

When the above procedure is followed using 1-(2,6-dimethylphenyl)-3-methylguanidine and 1-(2,6-dimethylphenyl)-1,3-dimethylguanidine then the products prepared are 1-(2,6-dimethylphenylamidino)-1-methylurea and 1-(2,6-dimethylphenyl-N-methylamidino)-1-methylurea.

When the above precedure is followed using the guanidines of Examples 2, 3 and 5, then the corresponding products are prepared.

EXAMPLE 8

1-(2,6-dimethylphenyl)-3-carbamylthiourea 1-(2,6-dimethylphenyl)-3-(t-butylcarbamyl)thiourea To a mixture of 8.8 g. (0.05 mole) of 1-(2,6-dimethylphenyl)thiourea and 10 ml. of xylene is added 5 g. of t-butylisocyanate (0.05 mole) and the mixture is refluxed for 2 hours. The reaction product is cooled, triturated with heptane and filtered. Recrystallization from 1:1 isopropanol/water results in 1-(2,6-dimethylphenyl)-3-(t-butylcarbamyl) thiourea.

1-(2,6-dimethylphenyl)-3-carbamylthiourea

A mixture of 25.6 g. (0.1 mole) of 1-(2,6-dimethylphenyl)-3-(t-butylcarbamyl)thiourea and 200 ml. of conc. hydrochloric acid is refluxed for ½ hour. The reaction mixture is cooled, the solid filtered and washed with 10 ml. of 1:1 HCl/H$_2$O and dried. The product is then recrystallized from ethanol-ether to obtain 1-(2,6-dimethylphenyl-3-carbamylthiourea.

When the above procedure is followed using 1-(2,6-dimethylphenyl)-1-methylthiourea; 1-(2,6-dimethylphenyl)-3-methylthiourea; 1-(2,6-dichlorophenyl)-1,3-dimethylthiourea; 1-(p-fluorophenyl)-3-methylthiourea then the products obtained are 1-(2,6-dimethylphenyl)-1-methyl-3-carbamylthiourea; 1-(2,6-dimethylphenyl)-3-methyl-3-carbamylthiourea; 1-(2,6-dimethylphenyl)-1,3-dimethyl-3-carbamylthiourea; and 1-(p-fluorophenyl)-3-carbamylthiourea.

When the above procedure is followed using the thiourea compounds of Examples 4 and 5 then the corresponding product is obtained.

When the above procedure is followed using the substituted isocyanate compounds of Table II, Example 6, then the corresponding product is obtained.

When the above procedure is followed using the thiourea compounds of Examples 4 and 5 and the substituted isocyanate compounds of Table II, Example 6, then the corresponding product is obtained.

EXAMPLE 9

1-(2,6-dimethylphenyl-N'-methylamidine)urea 1-(2,6-dimethylphenyl)-3-carbamyl-2-methylisothiouronium iodide 21.1 g. (0.1 mole) of 1-(2,6-dimethylphenyl-3-carbamylthiourea is combined with 200 ml. of methanol and 14.1 g. (0.1 mole) of iodomethane and refluxed for 4 hours. This is then evaporated to dryness and 100 ml. of hexane is added. The mixture is filtered to obtain 1-(2,6-dimethylphenyl)-3-carbamyl-3-methylisothiouronium iodide.

1-(2,6-dimethylphenyl-N'-methylamidino)urea 32.4 g. of 1-(2,6-dimethylphenyl)-3-carbamyl-2-methylisothiouronium iodide (0.1 mole) is added to 300 ml. of n-butanol. Methylamine gas is bubbled through this solution while refluxing for 24 hours. The reaction mixture is evaporated to dryness and extracted with 10% sodium hydroxide solution and ether. The ether is washed with 10% sodium hydroxide and then with water; dried and filtered. To this is added ethereal HCl and the precipitate is collected to obtain 1-(2,6-dimethylphenyl-N'-methylamidino)urea hydrochloride.

The free base is prepared by dissolving the above hydrochloride in 10% sodium hydroxide solution and extracting with ether. The ether is dried and evaporated to dryness to obtain 1-(2,6-dimethylphenyl-N'-methylamidino)urea.

When the above procedure is followed using the thiourea compounds prepared by Example 8, then the corresponding amidinourea is prepared.

When the above procedure is followed and methylamine is replaced with the amines of Table I, Example 5, then the coresonding product is obtained.

When the above procedure is followed using the thiourea compounds prepared by Example 8 and the amines of Table I, Example 5, then the coresonding product is prepared.

EXAMPLE 10

1-(2,6-dimethylphenylamidino)-3,3-($\alpha,\alpha'$-dimethylpentamethylene)urea

A. 2,6-dimethylpiperidinoyl chloride

To a solution of 50 g. of 2,6-dimethylpiperidine in 300 ml. of benzene is added 60 g. of phosgene and the mixture is refluxed for 3 hours. The solid which had separated was filtered and the filtrate was concentrated and distilled under vacuum to obtain 2,6-dimethylpiperidinoyl chloride.

B.
1-(2,6-dimethylphenylamidino)-3,3-($\alpha,\alpha'$-dimethylpentamethylene)urea To a mixture of 16.3 g. (0.1 mole) of 2,6-dimethylphenylguanidine in 250 ml. of dimethylformamide is added dropwise with stirring a solution of 17.5 g. (0.1 mole) of 2,6-dimethylpiperidinoyl chloride in 150 ml. of tetrahydrofuran. The mixture is stirred for 6 hours, poured onto ice, acidified with conc. HCl basified with sodium hydroxide and extracted with ether. The ether is washed with water and saturated sodium chloride solution and dried over magnesium sulfate. The filtered solution is evaporated to dryness to obtain 1-(2,6-dimethylphenyl)-3,3-($\alpha,\alpha'$-dimethylpentamethylene)urea.

The hydrochloride salt is prepared by dissolving the above free base in ether and adding ethereal hydrochloric acid. The formed hydrochloride is separated and recrystallized from acetonitrile/water/conc. HCl.

When 2,6-dimethylpiperidine is replaced in the above example by the amines of Table I below, then the corresponding product is prepared.

Table 1

|  |
| --- |
| piperidine |
| 4-methylpiperidine |
| N-methylpiperazine |
| N-methylhomopiperazine |
| morpholine |
| thiazolidine |
| octamethyleneamine |
| 2-methylazacyclooctane |
| pyrrolidine |
| dimethylamine |
| diethylamine |
| methylethylamine |
| ethylpropylamine |
| ethylcyclopropylamine |
| ethylbenzylamine |
| dibenzylamine |
| dicyclopropylamine |
| methylcyclobutylamine |
| methyl-t-butylamine |
| ethyl-t-butylamine |
| cyclopropyl-t-butylamine |
| methyl(cyclopropylmethyl)amine |

When 2,6-dimethylphenylguanidine in the above Example is replaced by the guanidines prepared in Examples 1, 2, 3 and 5, then the corresponding product is obtained.

When the above procedure is followed, and 2,6-dimethylphenylguanidine is replaced by the guanidines of Examples 1, 2, 3 and 5 and 2,6-dimethylpiperidine is replaced by the amines of Table I above, then the corresonding product is prepared.

EXAMPLE 11

1-(2,6-dimethylphenyl-N'-methylamidino)-3,3-diethylurea

A. 1-(2,6-dimethylphenyl)-3,3-diethylcarbamylthiourea

To a mixture of 8.8 g. (0.05 mole) of 1-(2,6-dimethylphenyl) thiourea in 150 ml. of dimethylformamide is added dropwise with stirring a solution of 6.75 g. (0.01 mole) of diethylcarbamyl chloride in 100 ml. of tetrahydrofuran (prepared from diethylamine and phosgene according to Example 10). The mixture is stirred for 10 hours, poured onto ice, acidified with conc. HCl while keeping the mixture at ice temperature and basified with sodium hydroxide and extracted with ether. The ether is washed, dried and evaporated to obtain 1-(2,6-dimethylphenyl)-3,3-diethylcarbamylthiourea.

B.
1-(2,6-dimethylphenyl)-3-(N,N-diethylcarbamyl)-2-methylthiouronium iodide (0.1 mole) of 1-(2,6-dimethylphenyl)-3-(N,N-diethylcarbamyl) thiourea is combined with 200 ml. of methanol and 14.1 g. (0.1 mole) of iodomethane and refluxed for 4 hours. This is then evaporated to dryness and 100 ml. of hexane is added. The mixture is filtered to obtain 1-(2,6-dimethylphenyl)-3-(N,N-diethylcarbamyl)-2-methylthiouronium iodide.

C.
1-(2,6-dimethylphenyl-N'-methylamidino)-3,3-diethylurea (0.1 mole) of 1-(2,6-dimethylphenyl)-3-(N,N-diethylcarbamyl)-2-methylthiouronium iodide (0.1 mole) is added to 300 ml. of n-butanol. Methylamine gas is bubbled through this solution while refluxing for 24 hours. The reaction mixture is evaporated to dryness and extracted with 10% sodium hydroxide solution and ether. The ether is washed with 10% sodium hydroxide and then with water; dried filtered and evaporated to dryness to obtain 1-(2,6-dimethylphenyl-N'-methylamidino)-3,3-diethylurea.

The hydrochloride salt is prepared by dissolving the above free base in ether and adding ethereal hydrochloric acid. The formed hydrochloride is separated and recrystallized from acetonitrile/water conc. HCl.

When diethylamine is replaced in the above example by the amines of Table I, Example 10, then the coresonding product is obtained.

When 1-(2,6-dimethylphenyl)thiourea is replaced with the thioureas prepared in Examples 4 and 5 then the corresponding product is obtained.

When 1-(2,6-dimethylphenyl)thiourea is replaced with the thioureas of Examples 4 and 5 and diethylamine is replaced by the amines of Table I, Example 10, then the corresponding product is obtained.

EXAMPLE 12

1-(2,6-Dimethylphenylamidino)urea hydrochloride

A mixture of 25.7 g. (0.106 moles) of 1-(2,6-dimethylphenylamidino)-3-(t-butyl)urea and 200 ml. of conc. hydrochloric acid is refluxed for ½ hour. The reaction mixture is cooled, the solid filtered and washed with 10 ml. of 1:1 HCl/H₂O and dried. The product is then recrystallized from ethanol-ether to obtain (2,6-dimethylphenylamidino)urea hydrochloride.

In a similar manner other desired salts may be prepared using the appropriate acid.

The free base is prepared according to Example 1.

When the above procedure is followed using the amidinoureas of Table I, Example 6, then the corresponding amidinourea of Table I is prepared as follows.

Table I 1-(m-chlorophenylamidino)urea
1-(p-chlorophenylamidino)urea
1-(2,3-dichlorophenylamidino)urea
1-(3,4-dichlorophenylamidino)urea
1-(3,5-dichlorophenylamidino)urea
1-(3,4,5-trichlorophenylamidino)urea
1-(m-bromophenylamidino)urea
1-(p-bromophenylamidino)urea
1-(2,5-dibromophenylamidino)urea
1-(3,4-dibromophenylamidino)urea
1-(3,5-dibromophenylamidino)urea
1-(3-chloro-4-bromophenylamidino)urea
1-(3-chloro-5-bromophenylamidino)urea
1-(4-chloro-3-bromophenylamidino)urea
1-(m-fluorophenylamidino)urea
1-(p-fluorophenylamidino)urea
1-(p-iodophenylamidino)urea
1-(3,4-difluorophenylamidino)urea
1-(3,5-difluorophenylamidino)urea
1-(3-fluoro-4-chlorophenylamidino)urea
1-(3-fluoro-5-chlorophenylamidino)urea
1-(3-chloro-4-fluorophenylamidino)urea
1-(3-fluoro-4-bromophenylamidino)urea
1-(3-bromo-4-fluorophenylamidino)urea
1-(3-chloro-4-iodophenylamidino)urea
1-(3-iodo-4-bromophenylamidino)urea
1-(3-iodo-4-chlorophenylamidino)urea
1-(3-bromo-4-iodophenylamidino)urea
1-(3-fluoro-4-iodophenylamidino)urea
1-(3-iodo-4-fluorophenylamidino)urea
1-(3,4-dimethoxyphenylamidino)urea
1-(3,4,5-trimethoxyphenylamidino)urea
1-(3,4-diethoxyphenylamidino)urea
1-(3,4,5-triethoxyphenylamidino)urea
1-(3-methoxy-4-chlorophenylamidino)urea
1-(3-chloro-4-methoxyphenylamidino)urea
1-(m-trifluoromethylphenylamidino)urea
1-(p-trifluoromethylphenylamidino)urea
1-(p-trifluoromethoxyphenylamidino)urea
1-(p-methylsulfonylphenylamidino)urea
1-(p-nitrophenylamidino)urea
1-(3-chloro-4-nitrophenylamidino)urea
1-(3-bromo-4-nitrophenylamidino)urea
1-(3-fluoro-4-nitrophenylamidino)urea
1-(3-nitro-4-chlorophenylamidino)urea
1-(3-nitro-4-bromophenylamidino)urea
1-(3-nitro-4-fluorophenylamidino)urea
1-(3-chloro-4-trifluoromethylphenylamidino)urea
1-(3-bromo-4-trifluoromethylphenylamidino)urea
1-(3-fluoro-4-trifluoromethylphenylamidino)urea
1-(3-chloro-4-methoxyphenylamidino)urea
1-(3-chloro-4-cyanophenylamidino)urea
1-(2-methyl-3-chlorophenylamidino)urea
1-(2-methyl-4-chlorophenylamidino)urea
1-(2-methyl-5-chlorophenylamidino)urea
1-(2-methyl-3-bromophenylamidino)urea
1-(2-methyl-4-bromophenylamidino)urea
1-(2-methyl-5-bromophenylamidino)urea
1-(2-methyl-3-fluorophenylamidino)urea
1-(2-methyl-4-fluorophenylamidino)urea
1-(2-methyl-5-fluorophenylamidino)urea
1-(2-methyl-4-nitrophenylamidino)urea
1-(2-methyl-4-cyanophenylamidino)urea
1-(2-methyl-4-trifluoromethylphenylamidino)urea
1-(2-methyl-5-trifluoromethylphenylamidino)urea
1-(2-methyl-6-ethylphenylamidino)urea
1-(2-methyl-6-propylphenylamidino)urea
1-(2,6-diethylphenylamidino)urea
1-(2-methyl-6-methoxyphenylamidino)urea
1-(2-methyl-6-ethoxyphenylamidino)urea
1-(2-ethyl-6-methoxyphenylamidino)urea
1-(2-ethyl-6-ethoxyphenylamidino)urea
1-(2-methyl-3,4-dichlorophenylamidino)urea
1-(2-methyl-3,5-dichlorophenylamidino)urea
1-(2-methyl-3,4,5-trichlorophenylamidino)urea
1-(2-methyl-3,5-dichloro-4-bromophenylamidino)urea
1-(2,6-dimethyl-3-chlorophenylamidino)urea
1-(2,6-dimethyl-4-chlorophenylamidino)urea
1-(2,6-dimethyl-3-bromophenylamidino)urea
1-(2,6-dimethyl-3-fluorophenylamidino)urea
1-(2,6-dimethyl-4-bromophenylamidino)urea
1-(2,6-dimethyl-4-fluorophenylamidino)urea
1-(2,6-diethyl-3-chlorophenylamidino)urea
1-(2,6-diethyl-4-chlorophenylamidino)urea
1-(2,6-dimethyl-3,4-dichlorophenylamidino)urea
1-(2,6-dimethyl-3,5-dichlorophenylamidino)urea
1-(2,6-dimethyl-3,4,5-trichlorophenylamidino)urea
1-(3-trifluoromethyl-4-methylphenylamidino)urea
1-(2,6-dimethyl-4-trifluoromethylphenylamidino)urea
1-(2-ethyl-4-nitrophenylamidino)urea
1-(2-ethyl-4-chlorophenylamidino)urea
1-(2-ethyl-4-bromophenylamidino)urea
1-(2-ethyl-4-fluorophenylamidino)urea
1-(2-ethyl-4-trifluoromethylphenylamidino)urea
1-(2,4-dichloro-6-methylphenylamidino)urea
1-(2,6-dichloro-4-methylphenylamidino)urea
1-(2,4-dibromo-6-methylphenylamidino)urea
1-(2,6-dibromo-4-methylphenylamidino)urea
1-(2-chloro-4-methyl-6-fluorophenylamidino)urea
1-(2,4-dimethyl-6-chlorophenylamidino)urea
1-(2,4-dimethyl-6-fluorophenylamidino)urea
1-(2-chloro-4-fluoro-6-methylphenylamidino)urea
1-(3,4-dibenzyloxyphenylamidino)urea

Example 13

Following the procedures of Examples 1–11, the following representative compounds may be prepared to demonstrate this invention.

| Starting Materials | Products | Ex. |
|---|---|---|
| 2,6-dimethylphenylguanidine + methylisocyanate | 1-(2,6-dimethylphenylamidino)-3-methylurea | 6 |
| 2,6-dimethylphenylguanidine + ethylisocyanate | 1-(2,6-dimethylphenylamidino)-3-ethylurea | 6 |
| 2,6-dimethylphenylguanidine + propylisocyanate | 1-(2,6-dimethylphenylamidino)-3-propylurea | 6 |
| 2,6-dimethylphenylguanidine + i-propylisocyanate | 1-(2,6-dimethylphenylamidino)-3-i-propylurea | 6 |

Example 13-continued

Following the procedures of Examples 1-11, the following representative compounds may be prepared to demonstrate this invention.

| Starting Materials | Products | Ex. |
|---|---|---|
| 2,6-dimethylphenylguanidine + butylisocyanate | 1-(2,6-dimethylphenylamidino)-3-butylurea | 6 |
| 2,6-dimethylphenylguanidine + pentylisocyanate | 1-(2,6-dimethylphenylamidino)-3-pentylurea | 6 |
| 2,6-dimethylphenylguanidine + cyclopropylisocyanate | 1-(2,6-dimethylphenylamidino)-3-cyclopropylurea | 6 |
| 2,6-dimethylphenylguanidine + cyclobutylisocyanate | 1-(2,6-dimethylphenylamidino)-3-cyclobutylurea | 6 |
| 2,6-dimethylphenylguanidine + cyclopentylisocyanate | 1-(2,6-dimethylphenylamidino)-3-cyclopentylurea | 6 |
| 2,6-dimethylphenylguanidine + cyclohexylisocyanate | 1-(2,6-dimethylphenylamidino)-3-cyclohexylurea | 6 |
| 2,6-dimethylphenylguanidine + benzylisocyanate | 1-(2,6-dimethylphenylamidino)-3-benzylurea | 6 |
| 2,6-dimethylphenylguanidine + phenethylisocyanate | 1-(2,6-dimethylphenylamidino)-3-phenethylurea | 6 |
| 2,6-dimethylphenylguanidine + cyclopropylmethylisocyanate | 1-(2,6-dimethylphenylamidino)-3-cyclopropylmethylurea | 6 |
| 2,6-dimethylphenylguanidine + cyclobutylmethyisocyanate | 1-(2,6-dimethylphenylamidino)-3-cyclobutylmethylurea | 6 |
| 2,6-dimethylphenylguanidine + cyclopropylethylisocyanate | 1-(2,6-dimethylphenylamidino)-3-cyclopropylethylurea | 6 |
| 2,6-dimethylphenylguanidine + piperidinoyl chloride | 1-(2,6-dimethylphenylamidino)-3,3-pentamethyleneurea | 10 |
| 2,6-dimethylphenylguanidine + 4-methylpiperidinoyl chloride | 1-(2,6-dimethylphenylamidino)-3,3-(γ-methylpentamethylene)urea | 10 |
| 2,6-dimethylphenylguanidine + N-methylpiperazinoyl chloride | 1-(2,6-dimethylphenylamidino)-3,3-(N-methyl-3'-azapentamethylene)urea | 10 |
| 2,6-dimethylphenylguanidine + N-methylhomopiperazinoyl chloride | 1-(2,6-dimethylphenylamidino)-3,3-(N-methyl-3'-azapentamethylene)urea | 10 |
| 2,6-dimethylphenylguanidine + morpholinoyl chloride | 1-(2,6-dimethylphenylamidino)-3,3-(3'-oxapentamethylene)urea | 10 |
| 2,6-dimethylphenylguanidine + thiazolidinoyl chloride | 1-(2,6-dimethylphenylamidino)-3,3-(2'-thiatetramethylene)urea | 10 |
| 2,6-dimethylphenylguanidine + pyrrolidinoyl chloride | 1-(2,6-dimethylphenylamidino)-3,3-tetramethyleneurea | 10 |
| 2,6-dimethylphenylguanidine + N,N-dimethylcarbamyl chloride | 1-(2,6-dimethylphenylamidino)-3,3-dimethylurea | 10 |
| 2,6-dimethylphenylguanidine + N,N-diethylcarbamyl chloride | 1-(2,6-dimethylphenylamidino)-3,3-diethylurea | 10 |
| 2,6-dimethylphenylguanidine + N-ethyl-N-methylcarbamyl chloride | 1-(2,6-dimethylphenylamidino)-3-ethyl-3-methylurea | 10 |
| 2,6-dimethylphenylguanidine + N-ethyl-N-propylcarbamyl chloride | 1-(2,6-dimethylphenylamidino)-3-ethyl-3-propylurea | 10 |
| 2,6-dimethylphenylguanidine + N-cyclopropyl-N-ethylcarbamyl chloride | 1-(2,6-dimethylphenylamidino)-3-cyclopropyl-3-ethylurea | 10 |
| 2,6-dimethylphenylguanidine + N-benzyl-N-ethylcarbamyl chloride | 1-(2,6-dimethylphenylamidino)-3-benzyl-3-ethylurea | 10 |
| 2,6-dimethylphenylguanidine + N,N-dibenzylcarbamyl chloride | 1-(2,6-dimethylphenylamidino)-3,3-dibenzylurea | 10 |
| 2,6-dimethylphenylguanidine + N,N-dicyclopropylcarbamyl chloride | 1-(2,6-dimethylphenylamidino)-3,3-dicyclopropylurea | 10 |
| 2,6-dimethylphenylguanidine + N-cyclobutyl-N-methylcarbamyl chloride | 1-(2,6-dimethylphenylamidino)-3-cyclobutyl-3-methyl | 10 |
| 1-(2,6-dimethylphenyl)-1-methylguanidine + methylisocyanate | 1-(2,6-dimethylphenyl-N-methylamidino)-3-methylurea | 7 |
| 1-(2,6-dimethylphenyl)-3-(N-methylcarbamyl)-2-methylisothiouronium iodide + methylamine | 1-(2,6-dimethylphenyl-N'-metylamidino)-3-methylurea | 9 |
| 1-(2,6-dimethylphenyl)-3-(N-t-butylcarbamyl)-2-methylisothiouronium iodide + methylamine | 1-(2,6-dimethylphenyl-N'-methylamidino)-3-t-butylurea | 9 |
| 1-(2,6-dimethylphenyl)-3-methylguanidine + methylisocyanate | 1-(2,6-dimethylphenylamidino)-1,3-dimethylurea | 6 |
| 1-(2,6-dimethylphenyl)-3-methylguanidine + t-butylisocyanate | 1-(2,6-dimethylphenylamidino)-1-methyl-3-t-butylurea | 6 |
| 1-(2,6-dimethylphenyl)-1,3-dimethylguanidine + t-butylisocyanate | 1-(2,6-dimethylphenyl-N-methylamidino)-1-methyl-3-t-butylurea | 6 |
| 1-(2,6-dimethylphenyl)-3-methyl-3-(N-t-butylcarbamyl)-2-methylisothiouronium iodide) + methylamine | 1-(2,6-dimethylphenyl-N'-methylamidino)-1-methyl-3-t-butylurea | 9 |
| 1-(2,6-dimethylphenyl)-1,3-dimethyl-3-(N-t-butylcarbamyl)-2-methylisothiouronium iodide) + methylamine | 1-(2,6-dimethylphenyl-N,N'-dimethylamidino)-1-methyl-3-t-butylurea | 9 |
| 1-(2,6-dimethylphenyl)-1,3-dimethyl-3-(N-methylcarbamyl)-2-methylisothiouronium iodide) + methylamine | 1-(2,6-dimethylphenyl-N,N'-dimethylamidino)-1,3-dimethylurea | 9 |
| p-fluorophenylguanidine + methylisocyanate | 1-(p-fluorophenylamidino)-3-methylurea | 6 |
| 1-(p-chlorophenyl)-1-methylguanidine + t-butylisocyanate | 1-(p-chlorophenyl-N-methylamidino)-3-(t-butyl)urea | 7 |
| 1-(p-chlorophenyl-N-methylamidino)-3-(t-butyl)urea + conc. HCl | 1-(p-chlorophenyl-N-methylamidino)urea | 7 |
| 1-(p-chlorophenylamidino)-1-methyl-3-(t-butyl)urea + conc. HCl | 1-(p-chlorophenylamidino)-1-methylurea | 7 |
| 1-(p-chlorophenyl-N-methylamidino)-1-methyl-3-(t-butyl)urea + HCl | 1-(p-chlorophenyl-N-methylamidino)-1-methylurea | 7 |
| 1-(p-chlorophenyl)-3-carbamyl-2-methylisothiouronium iodide + methylamine | 1-(p-chlorophenyl-N'-methylamidino)urea | 9 |
| p-fluorophenylguanidine + 2,6-dimethylpiperidinoyl chloride | 1-(p-fluorophenylamidino)-3,3-(α,α'-dimethylpentamethylene)urea | 10 |
| 1-(p-fluorophenyl)-3-(N,N-diethylcarbamyl)-2-methylisothiouronium iodide + methylamine | 1-(p-fluorophenyl-N'-methylamidino)-3,3-diethylurea | |
| 1-(p-fluorophenyl)-3-(N-methylcarbamyl)-2-methylisothiouronium iodide + methylamine | 1-(p-fluorophenyl-N'-methylamidino)-3-methylurea | 9 |
| 1-(p-chlorophenyl)-3-methylguanidine + methylisocyanate | 1-(p-chlorophenylamidino)-1,3-dimethylurea | 6 |
| 1-(p-chlorophenyl)-3-methyl-3-(N-methylcarbamyl)-2-methylisothiouronium iodide + methylamine | 1-(p-chlorophenyl-N'-methylamidino)-1,3-dimethylurea | 9 |
| 1-(p-chlorophenyl)-1,3-dimethylguanidine + methylisocyanate | 1-(p-chlorophenyl-N-methylamidino)-1,3-dimethylurea | 6 |
| 1-(p-chlorophenyl)-1,3-dimethyl-3-(N-methylcarbamyl)-2-methylisothiouronium iodide + methylamine | 1-(p-chlorophenyl-N,N'-dimethylamidino)-1,3-dimethylurea | 9 |
| p-(chlorophenylguanidine + piperidinoyl chloride | 1-(p-chlorophenylamidino)-3,3-(pentamethylene)urea | 10 |
| 1-(3,4-dichlorophenyl-N-methylamidino-3-t-butyl)urea + conc. HCl | 1-(3,4-dichlorophenyl-N-methylamidino)-urea | 7 |
| 1-(p-bromophenyl)-3-methyl-3-carbamyl-2-methylisothiouronium iodide + methylamine | 1-(p-bromophenyl-N'-methylamidino)-1-methylurea | 9 |
| 1-(2-methyl-4-fluorophenyl)guanidine + ethylisocyanate | 1-(2-methyl-4-fluorophenylamidino)-3-ethylurea | 7 |
| 1-(p-trifluoromethylphenylamidino)-1-methyl-3-(t-butyl)urea + conc. HCl | 1-(p-trifluoromethylphenylamidino)-1-methylurea | 7 |
| p-trifluoromethylphenylguanidine + methylisocyanate | 1-(p-trifluoromethylphenylamidino)-3-methylurea | 6 |
| 1-(p-trifluoromethoxyphenyl-N-ethylamidino)-3-(t-butyl)urea + conc. HCl | 1-(p-trifluoromethoxyphenyl-N-ethylamidino)urea | 7 |
| p-methylsulfonylphenylguanidine + N,N-diethylcarbamyl chloride | 1-(p-methylsulfonylphenylamidino)-3,3-diethylurea | 10 |
| p-nitrophenylguanidine + ethylisocyanate | 1-(p-nitrophenylamidino)-3-ethylurea | 6 |
| 1-(2,6-diethylphenylamidino)-1-ethyl-3-t-butylurea + conc. HCl | 1-(2,6-diethylphenylamidino)-1-ethylurea | 7 |
| 1-(2-methyl-6-methoxyamidino)-1-ethyl-3-t-butylurea + conc. HCl | 1-(2-methyl-6-methoxyphenylamidino)-1-ethylurea | 7 |
| 1-(2-methyl-4-chlorophenyl-N-methylamidino)-3-t-butylurea + conc. HCl | 1-(2-methyl-4-chlorophenyl-N-methylamidino)urea | 7 |
| 1-(2-methyl-4-bromophenyl-N-methylamidino)-3-t-butylurea + conc. HCl | 1-(2-methyl-4-bromophenyl-N-methylamidino)urea | 7 |
| 1-(2-methyl-4-fluorophenyl-N-methylamidino)-3-t-butylurea | 1-(2-methyl-4-fluorophenyl-N-methylamidino)urea | 7 |

Example 13-continued

Following the procedures of Examples 1–11, the following representative compounds may be prepared to demonstrate this invention.

| Starting Materials | Products | Ex. |
|---|---|---|
| 1-(2,6-diethylphenyl-N-methylamidino)-3-t-butylurea + conc. HCl | 1-(2,6-diethylphenyl-N-methylamidino)urea | 7 |
| 1-(2-fluoro-4-methylphenyl-N-methylamidino)-3-t-butylurea + conc. HCl | 1-(2-fluoro-4-methylphenyl-N-methylamidino)urea | 7 |
| 1-(2-methyl-4-nitrophenyl-N-methylamidino)-3-t-butylurea + conc. HCl | 1-(2-methyl-4-nitrophenyl-N-methylamidino)urea | 7 |
| 1-(2-methyl-6-methyoxyphenyl-N-methylamidino)-3-t-butylurea + conc. HCl | 1-(2-methyl-6-methoxyphenyl-N-methylamidino)urea | 7 |
| 1-(2-methyl-6-ethylphenyl-N-methylamidino)-3-t-butylurea + conc. HCl | 1-(2-methyl-6-ethylphenyl-N-methylamidino)urea | 7 |
| 1-(2,6-dimethoxyphenyl-N-methylamidino)-3-t-butylurea + conc. HCl | 1-(2,6-dimethoxyphenyl-N-methylamidino)urea | 7 |
| 1-(2,6-dimethylphenyl-N-methylamidino)-3-t-butylurea + conc. HCl | 1-(2,6-dimethylphenyl-N-methylamidino)urea | 7 |
| 1-(3-trifluoromethyl-4-chlorophenyl-N-methylamidino)-3-t-butylurea + conc. HCl | 1-(3-trifluoromethyl-4-chlorophenyl-N-methylamidino)urea | 7 |
| 1-(2-methyl-4-trifluoromethylphenyl-N-methylamidino)-3-t-butylurea + conc. HCl | 1-(2-methyl-4-trifluoromethylphenyl-N-methylamidino)urea | 7 |
| 1-(2,4-dichloro-6-methylphenyl-N-methylamidino)-3-t-butylurea + conc. HCl | 1-(2,4-dichloro-6-methylphenyl-N-methylamidino)urea | 7 |
| 1-(2,6-diethyl-4-methylphenyl-N-methylamidino)-3-t-butylurea + conc. HCl | 1-(2,6-diethyl-4-methylphenyl-N-methylamidino)urea | 7 |
| 1-(2-methyl-4-chloro-6-ethylphenyl-N-methylamidino)-3-t-butylurea + conc. HCl | 1-(2-methyl-4-chloro-6-ethylphenyl-N-methylamidino)urea | 7 |
| 1-(2,6-dimethyl-4-chlorophenyl-N-methylamindino)-3-t-butylurea + conc. HCl | 1-(2,6-dimethyl-4-chlorophenyl-N-methylamidino)urea | 7 |
| 1-(2,6-dimethyl-4-fluorophenyl-N-methylamidino)-3-t-butylurea + conc. HCl | 1-(2,6-dimethyl-4-fluorophenyl-N-methylamidino)urea | 7 |
| 1-(2,4,6-trimethylphenyl-N-methylamidino)-3-t-butylurea + conc. HCl | 1-(2,4,6-trimethylphenyl-N-methylamidino)urea | 7 |
| 1-(3-chloro-4-methyl-5-fluorophenyl-N-methylamidino)-3-t-butylurea + conc. HCl | 1-(3-chloro-4-methyl-5-fluorophenyl-N-methylamidino)urea | 7 |
| 1-(2,6-dimethyl-4-nitrophenyl-N-methylamidino)-3-t-butylurea + conc. HCl | 1-(2,6-dimethyl-4-nitrophenyl-N-methylamidino)urea | 7 |
| 1-(2,6-dimethyl-4-fluorophenyl-N-methylamidino)-3-t-butylurea + conc. HCl | 1-(2,6-dimethyl-4-fluorophenyl-N-methylamidino)urea | 7 |
| 1-(2-chloro-4-fluoro-6-methylphenyl-N-methylamidino)-3-t-butylurea + conc. HCl | 1-(2-chloro-4-fluoro-6-methylphenyl-N-methylamidino)urea | 7 |
| 1-(3,4-dibenzyloxyphenylamidino)urea + Pd/C/ethanol | 1-(3,4-dihydroxyphenylamidino)urea | |
| 1-(3,4,5-tribenzyloxyphenylamidino)urea + Pd/C/ethanol | 1-(3,4,5-trihydroxyphenylamidino)urea | |
| 3,4-dibenzyloxphenylguanidine + methylisocyanate | 1-(3,4-dibenzyloxyphenylamidino/-3-methylurea | 7 |
| 3,4,5-tribenzyloxyphenylguanidine + methylisocyanate | 1-(3,4,5-tribenzyloxyphenylamidino)-3-methylurea | 7 |
| 1-(3,4-dibenzyloxyphenylamidino)-3-methylurea + Pd/C ethanol | 1-(3,4-dihydroxyphenylamidino)-3-methylurea | |
| 1-(3,4,5-tribenzyloxphenylamidino)-3-methylurea + Pd/C ethanol | 1-(3,4,5-trihydroxyphenylamidino)-3-methylurea | |

I claim:

1. A method for the treatment of diarrhea in humans and mammals which comprises the administering thereto between 0.01 to 500 mg/kg per day of a compound of the formula:

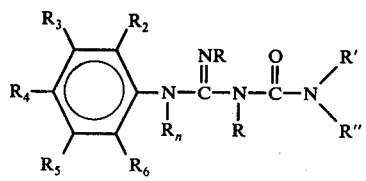

where:

$R_2$, $R_3$, $R_4$, $R_5$ and $R_6$ may be the same or different and are: hydrogen, halo, loweralkyl, haloloweralkyl, nitro, loweralkoxy, hydroxy, arloweralkoxy, acyloxy, cyano, haloloweralkoxy or loweralkylsulfonyl;

R and $R_n$ are hydrogen or loweralkyl; and

R' and R" together form a ring containing a group selected from the group consisting of tetramethylene, pentamethylene and hexamethylene 5-7 atom ring which may additionally include 0-2 hetero atoms of N,O or S; and the non-toxic acid addition salts thereof.

2. The method of claim 1 wherein said compound is 1-(2,6-dimethylphenylamidino-3,3-(N-methyl-3'-azapentamethylene)urea.

3. The method of claim 1 wherein said compound is 1-(2,6-dimethylphenylamidino)-3,3-(N-methyl-3'-azahexamethylene)urea.

4. The method of claim 1 wherein said compound is 1-(2,6-dimethylphenylamidino)-3,3-(3'-oxapentamethylene)urea.

5. The method of claim 1 wherein said compound is 1-(2,6-dimethylphenylamidino)-3,3-(2'-thiatetramethylene)urea.

6. The method of claim 1 wherein said compound is 1-(2,6-dimethylphenylamidino)-3,3-tetramethyleneurea.

7. The method of claim 1 wherein said compound is 1-(p-fluorophenylamidino)-3,3-(α, α'-dimethylpentamethylene)urea.

8. The method of claim 1 wherein said compound is 1-(p-chlorophenylamidino)-3,3-(pentamethylene)urea.

9. The method of claim 1 wherein said compound is 1-(2,6-dimethylphenylamidino)-3,3-(α, α'-dimethylpentamethylene)urea.

10. The method of claim 1 wherein said compound is 1-(2,6-dimethylphenylamidino)-3,3-pentamethyleneurea.

11. The method of claim 1 wherein said compound is 1-(2,6-dimethylphenylamidino)-3,3-(γ-methylpentamethylene)urea.

12. The method of claim 1 wherein R' and R" together form a ring containing a group selected from the group consisting of tetramethylene, pentamethylene and hexamethylene.

* * * * *